United States Patent [19]

Holtkamp

[11] Plant 4,533

[45] May 6, 1980

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "Optimara", Isselburg, Fed. Rep. of Germany

[21] Appl. No.: 2,052

[22] Filed: Jan. 8, 1979

[51] Int. Cl.[2] ..... A01H 5/00

[52] U.S. Cl. ..... Plt./69

[58] Field of Search ..... Plt./69

*Primary Examiner*—Robert E. Bagwill
*Assistant Examiner*—James R. Feyrer
*Attorney, Agent, or Firm*—Donald D. Jeffery

[57] ABSTRACT

An African Violet referred to by the cultivar name Nashville having compact and vigorous growth habits; red-purple, frilled, non-dropping flowers; strong and upright stems; relatively quick saleability due to its vigorous growth habit, and by its generally funnel-shaped leaves having light-green centers.

2 Drawing Figures

The present invention comprises a new and distinct cultivar of African Violet plant, botanically known as *Saintpaulia ionantha,* and hereinafter referred to by the cultivar name Nashville. The new cultivar was identified during the breeding and selection process by the designation d. 150/2 - 67/78.

Nashville is generally characterized by a very compact habit, leaves which are light green at the center and slightly wavy and serrated at the edges. Leaves with light green centers are commonly referred to as "girl" type leaves. The flowers are red-purple frilled, and are carried on strong upright stems. These traits in combination were not present in previously available commercial cultivars.

The new cultivar was originated from a cross made in a controlled breeding program in Isselburg, Rhineland, Germany. The female, or seed parent was 79 blue, a "girl" type cultivar of the type mentioned above. The male, or pollen parent was 17/75, a blue-violet cultivar known by the cultivar name Evelyn and disclosed in U.S. Plant Pat. No. 4,154.

The new cultivar Nashville was discovered and selected as a flowering plant within the progeny of the stated cross by me in a controlled environment in Isselburg, Rhineland, Germany.

Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Nashville, which in combination distinguish this African Violet as a new and distinct cultivar;

(1) Very compact habit.

(2) Red-purple, frilled edge flowers, non-dropping.

(3) Vigorous growth habit.

(4) Strong flower stems, with up to 8 flowers on each stem.

(5) Funnel-shaped leaves with light-green center.

The accompanying photographic drawing shows a typical specimen plant of the new cultivar. The colors appearing in the photograph are as true as possible with color illustrations of this type.

In the following description, color references are made to the Royal Horticultural Society (RHS) color chart, except where general color terms of ordinary significance are used.

Botanical classification: *Saintpaulia ionantha,* Ramat. cv Nashville.

Parentage:

*Male parent.*—17/75, U.S. Plant Pat. No. 3,154.

*Female parent.*—79 blue Girl.

Propagation: The new cultivar holds its distinguishing characteristics through successive propagations by leaf cuttings and by division of shoots.

Plant: From 8 cm to 10 cm tall when grown in pots, and approximately 20 cm in diameter when fully grown.

Leaves:

*General form.*—Oval-round.

*Diameter.*—50–65 mm.

*Texture.*—Soft-hairy.

*Aspect.*—Flat-funnel shaped.

*Veins.*—Light-green, well pronounced.

*Color (upperside).*—147 A.

*Color (underside).*—145 D.

*Petiole.*—Very strong; on upper side toward the leaf a 22 mm deep groove is clearly visible.

Flowers:

*Buds.*—Ball-shaped, 7–8 mm in diameter, color 70B.

*Sepals.*—Five; spear-shaped.

*Color.*—Brownish with greenish tips.

*Calyx.*—Grown together with torus.

*Aspect.*—Funnel-shaped.

*Peduncle.*—Red-brownish and hairy.

Individual Flowers:

*Size.*—42 mm in diameter and non-dropping.

*Color (upperside).*—72 A–B.

*Color (underside).*—72 C–D.

*Borne.*—Up to 7–8 flowers per stem.

*Shape.*—Five petals; two small, three large, all frilled.

*Corolla.*—The two small petals 17 mm long and 15 mm wide; the three large petals are 23 mm long and 19 mm wide.

*Arrangement.*—On very strong flower stems.

*Flowering time.*—7–8 weeks after potting appear the first flowers; full flower head appears in an additional 2–3 weeks.

Reproductive organs:

*Stamens.*—Two.

*Anthers.*—Four, color 7 B.

*Arrangement.*—Basifixed.

*Filaments.*—Yellow-greenish .

*Styles.*—Red-violet on light-green base.

*Pollen color.*—7 C.

*Roots.*—Young roots are white; when older turning brownish.

Disease resistance: Good, as experienced to date

General observations: Nashville is a vigorous growing variety. In a relative short growing period the plant is saleable with the first flash of flowers, a significant commercial factor. The habit is very compact and the flower stems are strong and upright. The flowers are frilled, red-purple, and non-dropping. The leaves with the light-green center are thicker than normal violet varieties.

I claim:

1. A new and distinct cultivar of African Violet, as described and illustrated, referred to by the cultivar name Nashville and particularly characterized by the combined features of compact and vigorous growth habits; red-purple, frilled, non-dropping flowers; strong and upright stems; relatively quick saleability due to its vigorous growth habit, and by its generally funnel-shaped leaves having light-green centers.

* * * * *

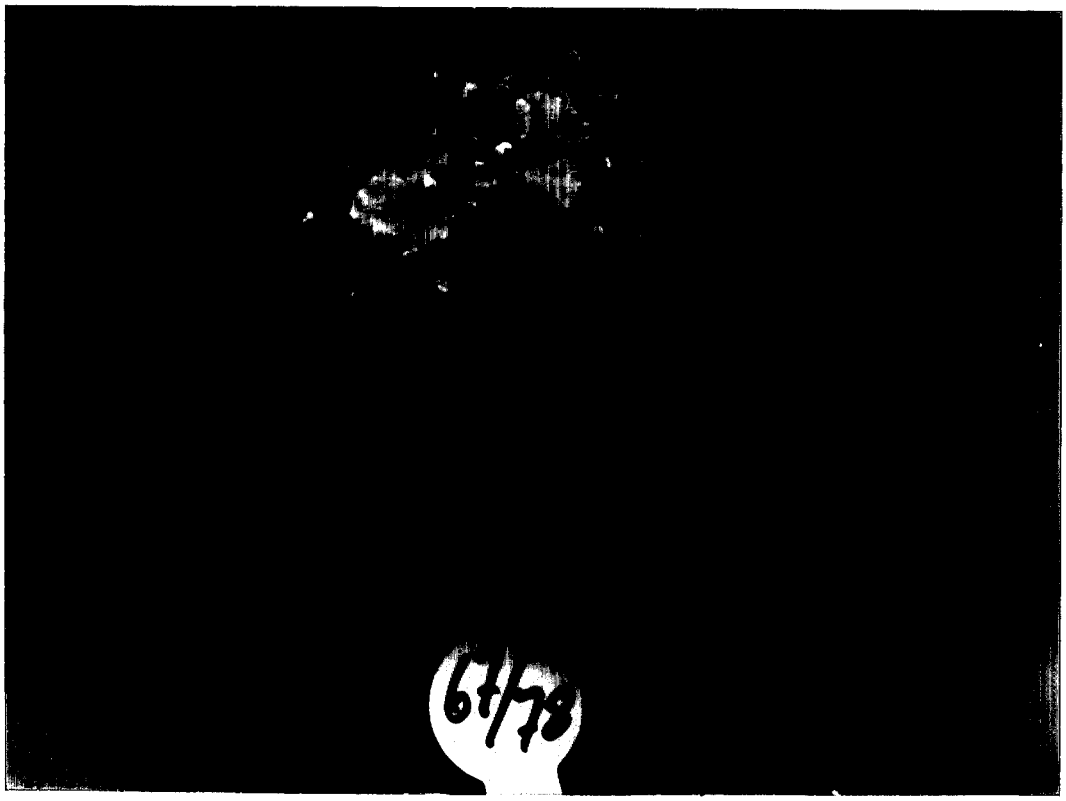
64/78